United States Patent
Cho et al.

(10) Patent No.: US 9,682,912 B2
(45) Date of Patent: Jun. 20, 2017

(54) METHOD FOR PREPARING LEVULINIC ACID USING SOLID ACID CATALYST IN PRESENCE OF ETHYLENE GLYCOL-BASED COMPOUND SOLVENT DERIVED FROM BIOMASS

(71) Applicant: KOREA INSTITUTE OF INDUSTRIAL TECHNOLOGY, Cheonan-Si, Chungcheongnam-Do (KR)

(72) Inventors: Jin Ku Cho, Yongin-si (KR); Sang Yong Kim, Cheonan-si (KR); Do Hoon Lee, Seoul (KR); Jae Won Jeong, Seoul (KR)

(73) Assignee: KOREA INSTITUTE OF INDUSTRIAL TECHNOLOGY, Cheonan-si (KR)

( * ) Notice: Subject to any disclaimer, the term of this patent is extended or adjusted under 35 U.S.C. 154(b) by 0 days.

(21) Appl. No.: 14/915,564

(22) PCT Filed: Aug. 28, 2014

(86) PCT No.: PCT/KR2014/008042
§ 371 (c)(1),
(2) Date: Feb. 29, 2016

(87) PCT Pub. No.: WO2015/030509
PCT Pub. Date: Mar. 5, 2015

(65) Prior Publication Data
US 2016/0221908 A1 Aug. 4, 2016

(30) Foreign Application Priority Data
Aug. 29, 2013 (KR) .................. 10-2013-0103058

(51) Int. Cl.
| | | |
|---|---|---|
| *C07C 51/00* | (2006.01) |
| *B01J 31/04* | (2006.01) |
| *C07C 51/573* | (2006.01) |
| *C07C 53/126* | (2006.01) |
| *B01J 21/18* | (2006.01) |
| *B01J 31/02* | (2006.01) |
| *B01J 31/08* | (2006.01) |

(52) U.S. Cl.
CPC ............... *C07C 51/00* (2013.01); *B01J 21/18* (2013.01); *B01J 31/0229* (2013.01); *B01J 31/04* (2013.01); *B01J 31/08* (2013.01); *C07C 51/573* (2013.01); *C07C 53/126* (2013.01); *B01J 2231/766* (2013.01); *B01J 2531/002* (2013.01); *Y02E 50/343* (2013.01)

(58) Field of Classification Search
CPC .................................................. C07C 51/573
USPC ........................................................ 562/515
See application file for complete search history.

(56) References Cited

FOREIGN PATENT DOCUMENTS

| | | |
|---|---|---|
| EP | 2233477 A1 | 9/2010 |
| JP | 2010150159 A | 7/2010 |
| JP | 2013103921 A | 5/2013 |
| KR | 100857914 A | 8/2008 |

OTHER PUBLICATIONS

M. Bruscino., Biorefineries:Facts or Fiction? Hydrocarbon Processing, 2009, pp. 65-68.
Xiao-Yan Liu et al., Preparation of a Carbon-Based Solid Acid Catalyst by Sulfonating Activated Carbon in a Chemical Reduction Process, Molecules, 2010,15(10), pp. 7188-7196.
Ji-Dong Chen et al., Preparation of 5-Hydroxymethyfurfural Via Fructose Acetonides in Ethelene Glycol Dimethyl Ether, Biomass & Bioenergy, vol. 1,No. 4, pp. 217-223, 1991.
P. A. Son, S. Nishimura, K. Ebitani, Synthesis of levulinic acid from fructose using Amberlyst-15 as a solid acid catalyst, Reac Kinet Mech Cat, 2012, vol. 106, pp. 185-192, Springer, Germany.

*Primary Examiner* — Sikarl Witherspoon
(74) *Attorney, Agent, or Firm* — STIP Law Group, LLC

(57) ABSTRACT

Provided is a method for preparing levulinic acid using a solid acid catalyst in the presence of an ethylene glycol-based compound. The levulinic acid according to the present invention can be prepared by using a linear or cyclic ethylene glycol-based compound as a solvent and preparing the levulinic acid from fructose in the presence of the solid acid catalyst at a reaction temperature of 100 to 200° C., thereby reducing the dependency on petroleum in response to greenhouse gas emission regulations. Also, a high yield of levulinic acid can be obtained from fructose, and the solvent and the catalyst can be efficiently separated, collected, and reused after the reaction has completed.

13 Claims, 1 Drawing Sheet

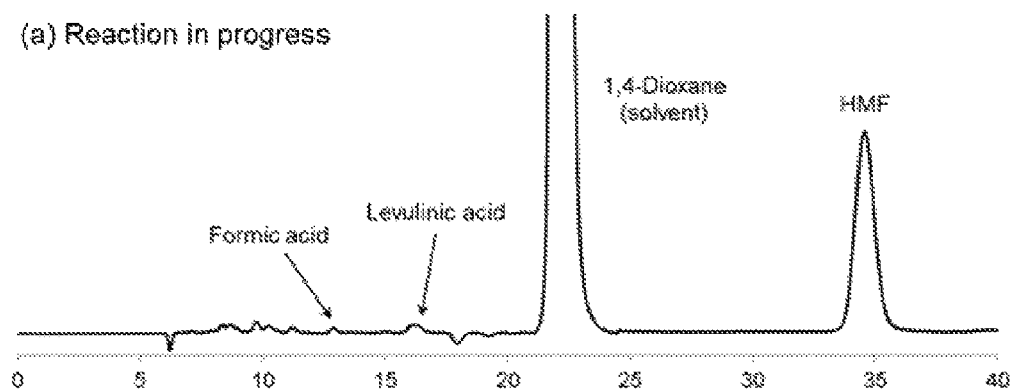
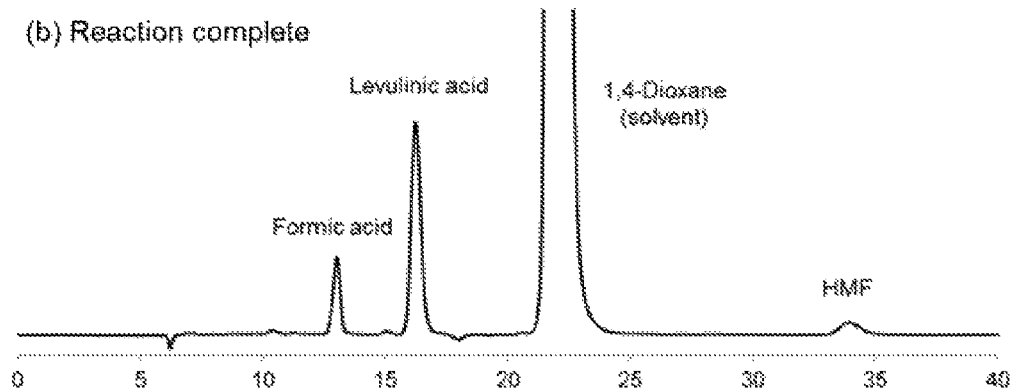

METHOD FOR PREPARING LEVULINIC ACID USING SOLID ACID CATALYST IN PRESENCE OF ETHYLENE GLYCOL-BASED COMPOUND SOLVENT DERIVED FROM BIOMASS

This is a U.S. national stage application of PCT Application No. PCT/KR2014/008042 under 35 U.S.C. 371, filed Aug. 28, 2014 in Korean, claiming the priority benefit of Korean Application No. 10-2013-0103058, filed Aug. 29, 2013, which is hereby incorporated by reference.

TECHNICAL FIELD

The present disclosure relates to the preparation of 5-levulinic acid. More particularly, the present disclosure relates to a method for preparing levulinic acid, a platform compound for high value-added biofuels or biochemicals, from fructose using a biomass-derived ethylene glycol-based solvent and a solid acid catalyst.

BACKGROUND ART

Because of their finite reserves, global petroleum resources are running out. With many developing countries currently industrializing, petroleum demand has sharply increased, causing an imbalance between market demand and supply and leading to an era of high oil prices. Furthermore, the reckless use of petroleum has brought about an explosive increase in greenhouse gases, provoking significant environmental problems such as global warming.

Extensive worldwide efforts have long been made to use biomass, which is regenerable and sustainable, as an alternative to petroleum resources. As a result, biofuels, such as bioethanol, biodiesel, etc. and bioplastic monomers, such as lactic acid, propanediol, etc., are successfully produced on an industrial scale and are used as substitutes for transportation fuels or petrochemical materials.

In recent years, intensive attention has been paid to levulinic acid as it has been discovered to be producible via conversion of biomass-derived carbohydrates.

During the dehydration, levulinic acid can be synthesized from hexoses via 5-hydroxymethyl-2-furfural (HMF) as an intermediate or from pentoses via furfural as an intermediate. Of carbohydrates, fructofuranose, an isomeric form of fructose, is most easy to convert into the intermediate 5-hydroxymethyl-2-furfural.

According to a report released by the U.S. Department of Energy (DOE), levulinic acid is one of the platform compounds chosen as "Top Value-Added Chemicals from Biomass", and can be converted into a wide spectrum of compounds including a monomer for polymers, a herbicide, a medicine, a flavoring agent, a solvent, a plasticizer, an antifreezing liquid, a fuel additive, etc. [(i) J. J. Bozell, G. R. Petersen, Green Chem. 2010, 12, 539-554; (ii) T. Werpy, G. R. Petersen, Top value-added chemicals from biomass volume I—Results of screening for potential candidates from sugars and synthesis gas: U.S. Department of Energy, NREL/TP-510-35523 (2004)]. However, industrial mass production of levulinic acid has not yet been achieved.

Levulinic acid is synthesized by dehydrating biomass-derived carbohydrates under an acidic condition. Typically, the dehydration is conducted by heating a carbohydrate in a 1-10% aqueous solution of an inorganic acid. The inorganic acid may be hydrogen chloride or sulfuric acid.

However, the use of such a homogenous inorganic acid as a catalyst entails problems in industrial application because the acid is difficult to remove from the solution after the dehydration, thus producing a great deal of highly concentrated waste water. That is, a significant portion of the production cost of levulinic acid is allocated to the treatment of the highly concentrated wastewater produced upon the use of the inorganic acid as a catalyst.

DISCLOSURE

Technical Problem

Accordingly, an object of the present disclosure is to provide a method for converting levulinic acid from fructose, the method employing a biomass-derived non-petroleum solvent, whereby dependence of the chemical industry on petroleum can be alleviated and the regulation of greenhouse gases can be achieved, at least in part. Also, the present disclosure provides a method for preparing levulinic acid from fructose at high yield, whereby the solvent and the catalyst can be effectively separated from each other after completion of the reaction, and thus can be reused.

Technical Solution

In order to accomplish the above object, the present disclosure provides a method for preparing levulinic acid, comprising converting fructose into levulinic acid in the presence of a solid acid catalyst in a linear or cyclic ethylene glycol-based compound as a solvent.

In some embodiments of the present disclosure, the linear ethylene glycol-based compound is represented by the following Structural Formula:

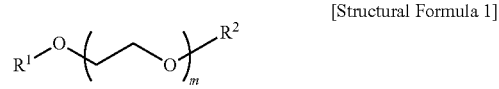

[Structural Formula 1]

wherein,
R$^1$ and R$^2$ may be the same or different and are each independently C1 to C6 alkyl, and
m is an integer of 1 to 6.

In some embodiments of the present disclosure, R$^1$ and R$^2$ may be the same or different and are each independently methyl or ethyl, and m is an integer of 1 to 4.

In some embodiments of the present disclosure, the cyclic ethylene glycol-based compound may be represented by the following Structural Formula 2:

[Structural Formula 2]

wherein,
n is an integer of 1 to 6.

In some embodiments of the present disclosure, n may be an integer of 1 to 3.

In some embodiments of the present disclosure, the linear or cyclic ethylene glycol-based compound may be derived from ethanol, the ethanol being prepared from biomass by fermentation.

In some embodiments of the present disclosure, the linear or cyclic ethylene glycol-based compound may be selected from a group consisting of 1,4-dioxane, monoethylene glycol dimethyl ether, diethylene glycol dimethyl ether, triethylene glycol dimethyl ether, tetraethylene glycol dimethyl ether, and combinations thereof.

In some embodiments of the present disclosure, the fructose may be provided as a fructose syrup having a water content of 10 to 50 weight parts per 100 weight parts of fructose.

In some embodiments of the present disclosure, the solid acid catalyst may be structured to have an organic or inorganic support to which a Brönsted acid or Lewis acid is linked as a functional group.

In some embodiments of the present disclosure, the organic support may be at least one selected from the group consisting of polystyrene, polyamide, and polyethylene glycol.

In some embodiments of the present disclosure, the inorganic support may comprise at least one selected from among silica, alumina, and zeolite.

In some embodiments of the present disclosure, the solid acid catalyst may contain amorphous carbon into which a sulfonic acid group has been introduced, the amorphous carbon being formed by incompletely carbonizing biomass.

In some embodiments of the present disclosure, the converting may be carried out at 120 to 180° C.

In some embodiments of the present disclosure, the method may further comprise recovering the solid acid catalyst from the solvent after the converting step.

Advantageous Effects

Featuring the employment of a biomass-derived non-petroleum solvent, the method for preparing levulinic acid in accordance with the present disclosure can alleviate the dependence of the chemical industry on petroleum and achieve the regulation of greenhouse gases, at least in part. In addition, 5-hydroxymethyl-2-furfural can be produced from fructose at high yield using the method, and the solvent and the catalyst can be effectively separated from each other by simple filtration after completion of the reaction, and thus can be reused.

DESCRIPTION OF DRAWINGS

FIG. 1 shows the change in an HPLC chromatogram throughout the preparation of levulinic acid as measured in Example 5.

BEST MODE

The embodiment of the present invention described hereinbelow is provided to allow those skilled in the art to more clearly comprehend the present invention.

However, it should be understood that the exemplary embodiments according to the concept of the present invention are not limited to the embodiments which will be described hereinbelow with reference to the accompanying drawings, but various modifications, equivalents, additions and substitutions are possible, without departing from the scope and spirit of the invention. In the following description, it is to be noted that, when the functions of conventional elements and the detailed description of elements related with the present invention may make the gist of the present invention unclear, a detailed description of those elements will be omitted.

The terminology used herein is for the purpose of describing particular embodiments only and is not intended to limit the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Below, embodiments of the present invention will be explained in detail. Therefore, the detailed description provided below should not be construed as being restrictive. In addition, the scope of the present invention is defined only by the accompanying claims and their equivalents if appropriate.

Unless defined otherwise, the term "alkyl", as used herein, refers to a linear, branched, or cyclic aliphatic hydrocarbon. The alkyl may be "saturated alkyl", free of double and triple bonds.

The alkyl may be "unsaturated alkyl" with at least one double or triple bond.

The alkyl may be C1 to C6 alkyl, and particularly C1 to C3 alkyl.

For example, C1 to C4 alkyl means an alkyl chain of 1 to 4 carbon atoms, such as methyl, ethyl, propyl, iso-propyl, n-butyl, iso-butyl, sec-butyl, and t-butyl.

Examples of the alkyl useful in the present disclosure include methyl, ethyl, propyl, isopropyl, butyl, isobutyl, t-butyl, pentyl, hexyl, ethenyl, propenyl, butenyl, cyclopropyl, cyclobutyl, cyclopentyl, and cyclohexyl.

In the method for preparing levulinic acid, fructose is dehydrated in the presence of the solid acid catalyst in a linear or cyclic ethylene glycol-based compound solvent at a reaction temperature of 100 to 200° C. to give levulinic acid.

The preparation mechanism of levulinic acid from fructose by dehydration is as illustrated in the following Reaction Scheme 1.

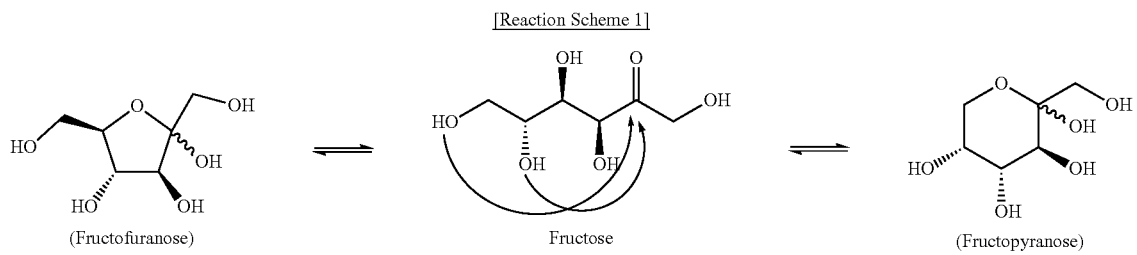

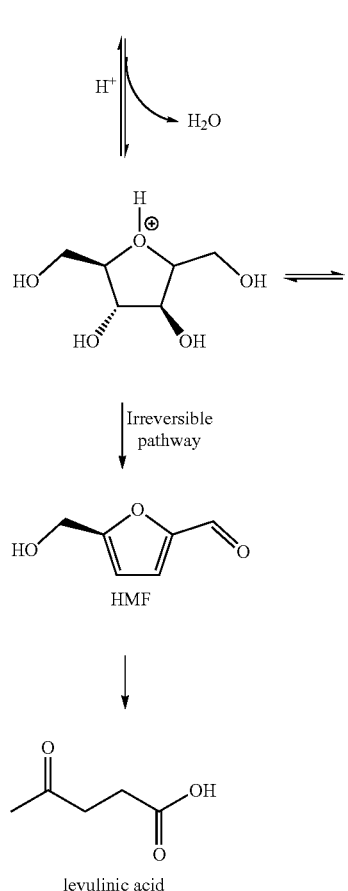

HMF levulinic acid

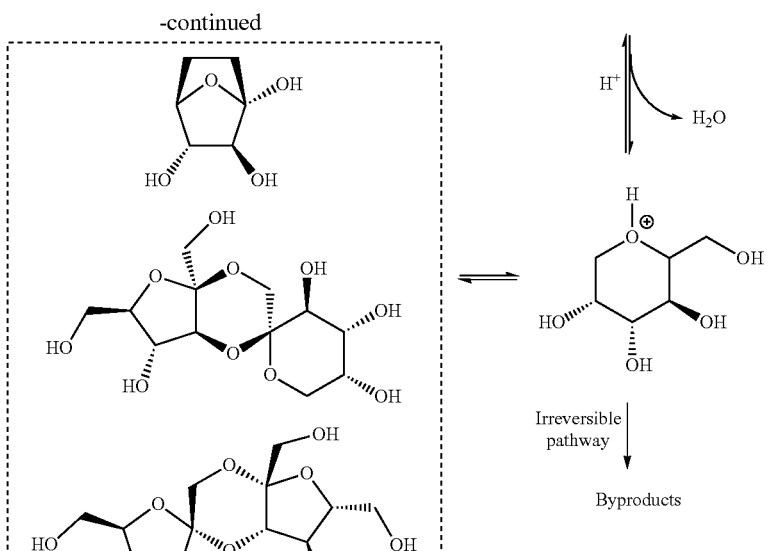

Intermediates

Serving as reversible fructose reservoirs during conversion from fructose into levulinic acid, the intermediate compounds of Reaction Scheme 1 can block the reaction from entering the fructopyranose pathway that leads to the production of undesired by-products such as humin.

The linear or cyclic ethylene glycol-based compound solvent is useful in stabilizing the intermediate compounds, thus contributing to the production of levulinic acid from fructose at high yield.

The dehydration may be conducted particularly at a temperature of 100 to 200° C., and more particularly at a temperature of 120 to 180° C.

At a temperature of less than 100° C., the production yield may be low because the reaction rate decreases, slowing conversion from the intermediate 5-hydroxymethyl-2-furfural to levulinic acid. On the other hand, a reaction temperature of higher than 200° C. increases the incidence of side reactions.

The reaction time may vary depending on the reaction temperature. A lower reaction temperature is associated with a longer reaction time. At a high reaction temperature, the reaction is conducted for a relatively short period of time. Briefly, the reaction time may be set to range from 0.5 to 15 hrs at a reaction temperature of 150° C., and particularly from 2 to 10 hrs. The reaction may be relatively lengthened at temperatures lower than 150° C. and shortened at temperatures higher than 150° C.

With regard to reaction pressure, the reaction can be carried out at atmospheric pressure when the reaction temperature is set to be less than the boiling point of a reaction solvent, which is convenient and economically beneficial. A reaction temperature higher than the boiling point of a reaction solvent requires a reaction apparatus that can endure the elevated pressure attributable to the vapor pressure of the solvent, but has the advantage of shortening the reaction time. Therefore, both the reaction pressure and the reaction temperature may be properly adjusted in response to the situation.

The linear ethylene glycol-based compound usefully available as a solvent may be represented by the following Structural Formula 1.

[Structural Formula 1]

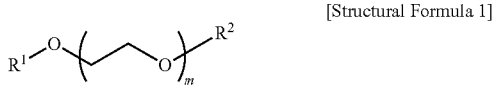

wherein, $R^1$ and $R^2$, which may be the same or different, are each independently C1 to C6 alkyl, and m is an integer of 1 to 6.

As can be seen in Structural Formula 1, the linear ethylene glycol-based compound solvent has a repeating ethylene glycol unit with the terminal hydroxy protected in the form of alkyl ether.

The number of the repeating ethylene glycol unit (m) may be 1 to 6, and particularly 1 to 4. If m is higher than 6, the production yield of levulinic acid may decrease and the solvent may be difficult to separate after completion of the reaction, thereby being difficult to recycle.

In addition, larger alkyl radicals ($R^1$ and $R^2$) are of higher hydrophobicity with less compatibility with fructose, and thus may be prone to decreasing the yield of levulinic acid.

$R^1$ and $R^2$ may be the same or different and are each independently C1 to C6 alkyl. In some embodiments of the present disclosure, $R^1$ and $R^2$ may the same or different and are each independently methyl or ethyl.

Further, the cyclic ethylene glycol-based compound available as the solvent may be a compound represented by the following Structural Formula 2:

[Structural Formula 2]

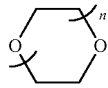

wherein,
n is an integer of 1 to 6.

The cyclic ethylene glycol-based compound useful as the solvent may have a cyclic molecular structure consisting of a repeating unit of ethylene glycol, as shown in Structural Formula 2.

Particularly, the number of repeating ethylene glycol units (n) may be 1 to 6, and more particularly 1 to 3. If n is greater than 6, the compound is too chemically unstable in an acidic condition to serve as a solvent.

For use as a biomass-derived solvent, the linear or cyclic ethylene glycol-based compound may be prepared from ethanol obtained through biomass fermentation. The mechanism for preparing the biomass-derived ethylene glycol-based compound is schematically illustrated in the following Reaction Scheme 2.

[Reaction Scheme 2]

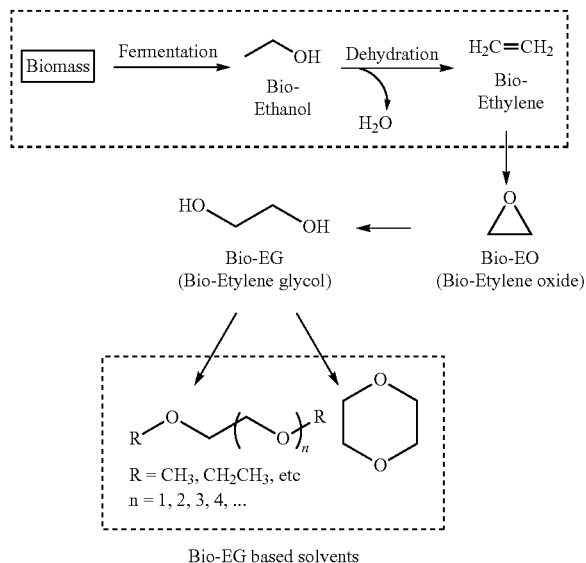

Bio-EG based solvents

Since it is derived from bio-ethanol, which is currently industrially produced, the ethylene glycol-based compound useful as a solvent in the present disclosure can be prepared at low cost and can decrease dependence on petroleum.

Examples of the linear or cyclic biomass-derived ethylene glycol-based compound useful as a solvent include 1,4-dioxane, monoethylene glycol dimethyl ether, diethylene glycol dimethyl ether, triethylene glycol dimethyl ether, and tetraethylene glycol dimethyl ether.

As for the solid acid catalyst, its structure is based on an organic or inorganic support to which a Brönsted acid or a Lewis acid is linked.

The organic support may be a polymer support comprising polystyrene, polyamide, polyethylene glycol, etc. The inorganic support may be based on silica, alumina, zeolite, etc.

As a catalytically active ingredient chemically linked to the support, the acid may be a Brönsted acid including sulfonic acid, phosphoric acid, etc., or a Lewis acid including a metal ion coordinated to a ligand.

Herein, the term "Brönsted acid" refers to a substance that donates a proton ($H^+$) in the context of an acid-base reaction, as defined by Brönsted-Lowry. The term "Lewis acid" means a substance that accepts an electron pair in an acid-base reaction, as defined by Lewis.

For use in the present disclosure, the solid acid catalyst may comprise a sulfuric acid that is introduced into an amorphous carbon support formed through incomplete carbonization of biomass.

The amorphous carbon can be obtained by incompletely carbonizing biomass. In some embodiments of the present disclosure, the biomass may be lignocellulosic biomass, examples of which include, but are not limited to, woods and rice straw. Particularly, the lignocellulosic biomass may contain lignin in an amount of 10 to 40 wt %.

The incomplete carbonization may be conducted chemically, using a dehydrating agent, or thermally. Thermal treatment for incomplete carbonization may be carried out at 400 to 600° C.

Subsequently, sulfuric acid comprising sulfur trioxide ($SO_3$) is added to the amorphous carbon to introduce sulfonic acid into the amorphous carbon. Particularly, the sulfuric acid contains sulfur trioxide in an amount of 15 to 50 wt %.

As prepared into an amorphous carbon form with sulfonic acid introduced thereinto, the solid acid catalyst may contain sulfonic acid in an amount of 0.4 to 0.8 mmol per gram of sulfonic acid.

For use in the present disclosure, the fructose is particularly in a syrup form containing water and fructose.

In this regard, the syrup particularly contains water in an amount of 10 to 50 weight parts based on 100 weight parts of fructose, and more particularly in an amount of 20 to 30 weight parts.

Because the ethylene glycol-based compound solvent used in the present disclosure is not completely miscible with water, fructose may not be used in the form of powder, but may be used mixed with water. Hence, an additional process of drying fructose is not needed.

A better understanding of the present invention may be obtained through the following examples which are set forth to illustrate, but are not to be construed as limiting the present invention.

EXAMPLES

Example 1

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent monoethylene glycol dimethyl ether (3 mL). The resulting solution was heated at 150° C. for 7 hrs while stirring at 700 rpm. After completion of the reaction, the reaction mixture was cooled to room temperature and diluted 100-fold in distilled water. HPLC analysis was conducted, indicating the production of levulinic acid at a yield of 43%.

Example 2

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent diethylene glycol dimethyl ether (3 mL). The resulting solution was heated at 150° C. for 4 hrs while stirring at 700 rpm. After completion of the reaction, the reaction mixture was cooled to room temperature, and diluted 100-fold in distilled water. HPLC analysis was conducted, indicating the production of levulinic acid at a yield of 62%.

Example 3

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent triethylene glycol dimethyl ether (3 mL). The resulting solution was heated at 150° C. for 3 hrs while stirring at 700 rpm. After completion of the reaction, the reaction mixture was cooled to room temperature and diluted 100-fold in distilled water. HPLC analysis was conducted, indicating the production of levulinic acid at a yield of 56%.

Example 4

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent tetraethylene glycol dimethyl ether (3 mL). The resulting solution was heated at 150° C. for 3 hrs while stirring at 700 rpm. After completion of the reaction, the reaction mixture was cooled to room temperature and diluted 100-fold in distilled water. HPLC analysis was conducted, indicating the production of levulinic acid at a yield of 51%.

Example 5

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent 1,4-dioxane (3 mL). The resulting solution was heated at 150° C. for 3 hrs while stirring at 700 rpm. After completion of the reaction, the reaction mixture was cooled to room temperature and diluted 100-fold in distilled water. HPLC analysis was conducted, indicating the production of levulinic acid at a yield of 71%.

Example 6

A solid acid catalyst was prepared by introducing sulfonic acid into amorphous carbon.

Briefly, 100 g of [EMIM]Cl was added to 10 g of wood in a 500 ml round-bottom flask. The mixture was heated at 120° C. while stirring at 650 rpm. The homogenized mixture was cooled to 10° C., followed by precipitation with ethanol. The precipitate was filtered, washed with water, and dried in vacuo. Subsequently, it was heated at 500° C. for 1 hr in a nitrogen atmosphere to give an amorphous carbon material.

The amorphous carbon material was treated with conc. $H_2SO_4$ (10%, wt/vol) while stirring at 80° C. for 2 hrs. Then, cooling, filtering, and washing with hot water were conducted, followed by additional washing with 1,4-dioxane in a Soxhlet extractor. Drying in a vacuum afforded a sulfonic acid-introduced carbon material.

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the biomass-derived amorphous carbon material (900 mg) having sulfonic acid introduced thereinto as a solid acid catalyst, followed by adding the EG-based solvent diethylene glycol dimethyl ether (3 mL). The resulting solution was heated at 150° C. for 10 hrs while stirring at 700 rpm. After completion of the reaction, the reaction mixture was cooled to room temperature, and diluted 100-fold in distilled water. HPLC analysis was conducted, indicating the production of levulinic acid at a yield of 55%.

Example 7

Levulinic acid was prepared as in Example 2, and the reaction mixture was cooled to room temperature and filtered. The filtrate was washed and dried in vacuo to recover the catalyst Amberlyst-15 while diethylene glycol dimethyl ether was separated and recycled by distillation.

Levulinic acid was prepared in the same manner as in Example 2, with the exception that the recovered Amberlyst-15 and monoethylene glycol dimethyl ether were used. After completion of the reaction, the reaction mixture was diluted 100-fold in distilled water. HPLC analysis was conducted, indicating the production of levulinic acid at a yield of 61%.

Comparative Example 1

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with Amberlyst-15 (300 mg) as a solid acid catalyst, followed by adding 1,3-dioxane (3 mL), which is similar in chemical structure to an EG-based solvent. The resulting solution was heated at 150° C. for 3 hrs while stirring at 700 rpm. After completion of the reaction, the reaction mixture was cooled to room temperature and diluted 100-fold in distilled water. HPLC analysis was conducted, indicating that almost no levulinic acid was produced and that 1,3-dioxane was decomposed in an acidic condition.

The levulinic acid preparation conditions and yields of Examples 1 to 7 and Comparative Example 1 are summarized in Table 1, below.

TABLE 1

| Ex. | Solvent | Catalyst | Rxn. Temp (°C.) | Rxn. Time (h) | Levulinic acid Yield (%) |
|---|---|---|---|---|---|
| Ex. 1 | monoethylene glycol dimethyl ether | Amberlyst-15 | 150 | 7 | 43 |
| Ex. 2 | diethylene glycol dimethyl ether | Amberlyst-15 | 150 | 4 | 62 |
| Ex. 3 | triethylene glycol dimethyl ether | Amberlyst-15 | 150 | 3 | 56 |
| Ex. 4 | tetraethylene glycol dimethyl ether | Amberlyst-15 | 150 | 3 | 51 |
| Ex. 5 | 1,4-dioxane | Amberlyst-15 | 150 | 3 | 71 |
| Ex. 6 | diethylene glycol dimethyl ether | Sulfone-introduced amorphous carbon | 150 | 10 | 55 |
| Ex. 7 | diethylene glycol dimethyl ether | Amberlyst-15 (recovered by separation) | 150 | 4 | 61 |
| C. Ex. 1 | 1,3-dioxane | Amberlyst-15 | 150 | 3 | 0 |

As is understood from the data of Table 1, levulinic acid was prepared at far higher yield in the manner described in one of Examples 1 to 7, compared to Comparative Example 1, in which no biomass-derived, ethylene glycol-based solvents were employed.

Test Example 1

HPLC (High Performance Liquid Chromatography) Analysis

HPLC chromatograms were read during the reaction (a) and at the time of completion of the reaction (b) in Example 5, as shown in FIG. 1.

As can be seen in FIG. 1, when the biomass-derived, ethylene glycol-based compound 1, 4-dioxane was employed, many intermediates were generated and then disappeared. As elucidated in conjunction with the dehydration mechanism above, the intermediates serve to block the progression of a pathway directing the conversion of fructose into by-products.

Also, the product prepared according to Example 5 was identified as levulinic acid by comparison with an authentic sample, as measured at the time of completion of the reaction using HPLC.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for preparing levulinic acid, comprising converting fructose into levulinic acid in the presence of a solid acid catalyst in a linear or cyclic ethylene glycol-based compound as a solvent, wherein the linear ethylene glycol-based compound is represented by the following Structural Formula 1:

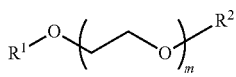

[Structural Formula 1]

wherein, $R^1$ and $R^2$ may be the same or different and are each independently C1 to C6 alkyl, and m is an integer of 1 to 6.

2. The method of claim 1, wherein $R^1$ and $R^2$ may be the same or different and are each independently methyl or ethyl, and m is an integer of 1 to 4.

3. The method of claim 1, wherein the cyclic ethylene glycol-based compound is represented by the following Structural Formula 2:

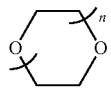

[Structural Formula 2]

wherein, n is an integer of 1 to 6.

4. The method of claim 3, wherein n is an integer of 1 to 3.

5. The method of claim 1, wherein the linear or cyclic ethylene glycol-based compound is derived from ethanol, the ethanol being prepared from biomass by fermentation.

6. The method of claim 1, wherein the linear or cyclic ethylene glycol-based compound is selected from a group consisting of 1,4-dioxane, monoethylene glycol dimethyl ether, diethylene glycol dimethyl ether, triethylene glycol dimethyl ether, tetraethylene glycol dimethyl ether, and a combination thereof.

7. The method of claim 1, wherein the fructose is provided as a fructose syrup having a water content of 10 to 50 weight parts per 100 weight parts of fructose.

8. The method of claim 1, wherein the solid acid catalyst is structured to have an organic or inorganic support to which a Brönsted acid or Lewis acid is linked as a functional group.

9. The method of claim 8, wherein the organic support is at least one selected from the group consisting of polystyrene, polyamide, and polyethylene glycol.

10. The method of claim 8, wherein the inorganic support comprises at least one selected from among silica, alumina, and zeolite.

11. The method of claim 1, wherein the solid acid catalyst contains amorphous carbon into which a sulfonic acid group is introduced, the amorphous carbon being formed by incompletely carbonizing biomass.

12. The method of claim 1, wherein the converting is carried out at 120 to 180° C.

13. The method of claim 1, further comprising recovering the solid acid catalyst from the solvent after the converting.

* * * * *